United States Patent [19]

Maspero et al.

[11] 4,100,208
[45] Jul. 11, 1978

[54] PROCESS FOR THE PRODUCTION OF UNSATURATED COMPOUNDS

[75] Inventors: Federico Maspero, Milan; Emilio Perrotti, S. Donato Milanese, both of Italy

[73] Assignee: Snam Progetti S.p.A., Milan, Italy

[21] Appl. No.: 460,222

[22] Filed: Apr. 11, 1974

Related U.S. Application Data

[63] Continuation of Ser. No. 147,653, May 27, 1971, abandoned.

[30] Foreign Application Priority Data

May 29, 1970 [IT] Italy .............................. 25267 A/70

[51] Int. Cl.$^2$ ............................................. C07C 29/00
[52] U.S. Cl. .................................... 568/902; 260/596; 568/813; 568/857; 568/903
[58] Field of Search ............. 260/596, 635 M, 642 R, 260/618 H, 642 E

[56] References Cited

U.S. PATENT DOCUMENTS

| | | | |
|---|---|---|---|
| 2,066,496 | 1/1937 | Taylor .................................. | 260/596 |
| 2,989,567 | 6/1961 | Leeds et al. ...................... | 260/618 H |
| 3,110,747 | 11/1963 | Mullineaux ...................... | 260/618 H |
| 3,458,547 | 7/1969 | Coffey ................................ | 260/596 |

*Primary Examiner*—Joseph E. Evans
*Attorney, Agent, or Firm*—Morgan, Finnegan, Pine, Foley & Lee

[57] ABSTRACT

Process for production of ethylenic compounds by hydrogenating the corresponding alkynol with isopropyl alcohol in the presence of a metal complex such as $IrH_3CO(P\phi_3)_2$ and $IrH_3(P\phi_3)_2$.

6 Claims, No Drawings

PROCESS FOR THE PRODUCTION OF UNSATURATED COMPOUNDS

This is a continuation of application Ser. No. 147,653, filed May 27, 1971, now abandoned.

The present invention refers to a process which allows one to obtain less unsaturated compounds starting from compounds with higher unsaturation.

It is known in organic chemistry that it is possible to reduce the unsaturation of a starting compound obtaining in such a way a less unsaturated compound. This is the case in the production of ethylenic compounds by hydrogenating acetylenic compounds or of saturated compounds starting from ethylenic or acetylenic compounds. It is known that said preparations are required in some particular cases, while generally the importance of compounds having greater unsaturations is higher because of their higher reactivity. In some cases, as aforesaid, and namely for the preparation of particular compounds, a hydrogenation of acetylenic compounds is effected to obtain the corresponding ethylenic compounds.

As examples of the above particular compounds the following may be cited: 3 methyl-1-butyn-3-ol, 2-butyn-1,4-diol, 1-butyn-3-ol, 3-phenyl-1-butyn-3-ol and so on. It is also known that such a way to effect the reaction requires particular operative conditions in order to obtain substantially the ethylene compound reducing as much as possible the saturated compound production due to the subsequent hydrogenation.

Ethynylation reactions are also known among which the one allowing one to obtain alkynols from carbonyl-containing and acetylenic compounds should be mentioned. Among the alkynols, it is known that methyl butynol which when hydrogenated and dehydrated yields isoprene which is a monomer of very high industrial interest since it may be used for the production of synthetic rubber having remarkable characteristics.

We have now found a simple and economic process which consists of transferring hydrogen from a compound capable to give it to another compound capable to accept said hydrogen. Such a second compound shall be defined in the present specification as "acceptor" and with such a term shall be defined any organic compound containing unsaturations as, for instance, a compound containing at least an acetylenic unsaturation or at least an ethylenic unsaturation or at least an acetylenic unsaturation with an ethylenic unsaturation. Said compound may also contain one or more functions. In the above-mentioned case, i.e. in the case of methyl butynol, a hydroxy function (alcoholic) is also pesent besides the acetylenic function.

The hydrogen transfer according to the invention takes place by means of particular compounds which in the specification shall be defined as hydrogen transfers. They are complex compounds of the metals belonging to the 8th group of the periodic table.

The preferred hydrogen transfers according to the invention are the complexes of mono- or trivalent rhodium, of mono- or trivalent iridium, of divalent ruthenium and of zero- or divalent platinum, of Fe, Ni, Co, Pd, at low oxidation stages. As complexing agent of the compounds of said metals the so-called low electronegative ones may be used.

Now-limitative examples of the above compounds are phosphines, namely triphenyl phosphine, carbon monoxide, carbonyls and nitrosyls, hydrides, arsines, stibines, olefins and substituted olefins. Non-limitative examples of the preferred complexes according to the invention are $IrH_3CO(P\phi_3)_2$ and $IrH_3(P\phi_3)_2$ (wherein $P\phi_3$ = triphenyl phosphine). As compounds capable to give hydrogen according to the invention shall be intended all the hydrocarbon compounds having the general formula:

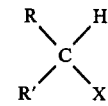

wherein R and R' represent simple or substituted hydrocarbon radicals as aliphatic, cyclic, cycloalkylic and aromatic; and X represents -OH, -OR or -OCOR wherein R has the above-mentioned meanings.

The compounds which correspond to the above formula are therefore alcohols, ethers or esters. The reaction takes place in absence of solvents since the mixture of the reagents may be used as reaction medium. A mixture 50/50 of two reagents is a good reaction medium. It is anyhow possible to solubilize the complex useful as catalyst, then introduce it into the reaction mixture. Therefore a class of solvents is the one known in the art to solubilize the employed complex. The reaction takes place in homogeneous phase and has, as aforesaid, a catalytic course.

The process according to the invention may be represented, in the case of the reaction of an acetylenic compound with an alcohol, in the following way:

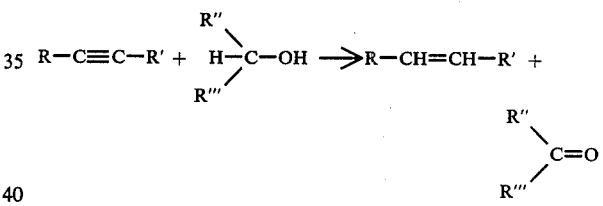

No limitations are provided as to the temperature; the temperature should be selected such to ensure the catalyst solution in the reaction medium, i.e. the homogenous phase, and in the same time to ensure a good kinetic.

Also for the pressure, no limitations are provided; the pressure is related to the temperature and should be such to ensure the maintenance of the liquid phase and to prevent the hydrogen from leaving the reaction system during the transfer. It is advantageous that the reaction is carried out in an inert atmosphere. The catalyst preparation is a conventional one. The reaction time depends on the kind of catalyst employed; some kinds of catalyst require only a few minutes while others require a longer time, up to several hours.

In order to better illustrate the invention, the following example is reported which is not to be intended as limitative thereof.

EXAMPLE 225 mg of $IrH_3(P\phi_3)_2$ were suspended in a well degassed mixture consisting of 13G of methylbutynol MBI and 15g of isopropyl alcohol. The flask was stoppered with two sealing ground stoppers, one of them being provided with a head of silicon rubber to enable the drawing of samples with a hypodermic syringe. The small flask was poured in a 80° C thermostated bath and the stirring was ensured with a magnetic stirrer. Periodically a sample pf 20 μl was drawn and was introduced into the gas chromatographic apparatus (Carlo Erba, Frattovap). The employed column was tricresylphosphate at 30% on Cromosorb W (4 meters) (60–80 mesh) (T=100° C, Tev. 200°, flow 30 cc/min).

Beside the peaks corresponding to the starting compounds (isopropylalcohol, $t_r=10'06''$, MBI, $Tr=35'30''$), the appearance of two more peaks was observed, identified to the mass spectrometer as acetone ($t_r=9'10''$ and methylbutenol) (MBE) ($tr=23'30''$). No other peaks were revealed. The amount of the obtained products has been determined from the area of peaks, in comparison with the standard sample of the same substance. At different times the amount of formed MBE results in grams:

time
0 : -
15' : 0.078
2hr.: 0.084
3hr.:0.086
6hr.: 0.093
12hr.: 0.106
24hr.: 0.120

As it is seen, the major part of the reaction takes place in the first minutes. The amount of formed acetone was equal on the molar basis to the one corresponding to the ethylenic compound. No formation of saturated compound was observed. The present example is well illustrative of the invention; it does not only show how the hydrogenation of an acetylenic to ethylenic compound takes place, but points out a particularly advantageous case of the stage of producing isoprene by ethynation.

In fact, according to the reaction of the example, methylbutenol was obtained which through dehydration produces isoprene, while isopropylic alcohol transforms to acetone which, by reacting with acetylene, yields methylbutynol. In such a way, as by product of the reaction of the example, a reactant of the ethynation reaction was obtained. The present example is not in any way limitative of the invention, the same procedure being indeed suitable in combination with other conventional procedures, if any, for other cases.

We claim:

1. Process for the selective production of an ethylenic compound by conversion of the corresponding acetylenic compounds which comprises reacting an acetylenic compound selected from the group consisting of 3-methyl-1-butyn-3-ol, 2-butyn-1,4-diol, 1-butyn-3-ol and 3-phenyl-1-butyn-3-ol with isopropyl alcohol in a homogeneous liquid phase in the presence of a metal complex selected from the group consisting of $IrH_3CO(P\phi_3)_2$ and $IrH_3(P\phi_3)_2$.

2. Process according to claim 1 wherein said acetylenic compound is 3-methyl-1-butyn-3-ol.

3. Process according to claim 1 wherein said metal complex is $IrH_3(P\phi_3)_2$.

4. Process according to claim 1 wherein said metal complex is $IrH_3CO(P\phi_3)_2$.

5. Process according to claim 1 wherein said acetylenic compound is 3-methyl-1-butynol and said metal complex is $IrH_3(P\phi_3)_2$.

6. Process according to claim 1 wherein a solvent is included.

* * * * *